(12) United States Patent
Herscheid et al.

(10) Patent No.: US 7,901,667 B2
(45) Date of Patent: Mar. 8, 2011

(54) BRIDGEHEAD LABELLED COMPOUNDS AND METHODS OF USING THE SAME

(75) Inventors: Jacobus Donatus M. Herscheid, Nieuw-Vennep (NL); Joost Verbeek, Enkhuizen (NL)

(73) Assignee: Mallinckrodt Inc., Hazelwood, MO (US)

( * ) Notice: Subject to any disclaimer, the term of this patent is extended or adjusted under 35 U.S.C. 154(b) by 549 days.

(21) Appl. No.: 11/815,237

(22) PCT Filed: Jan. 30, 2006

(86) PCT No.: PCT/US2006/003600
§ 371 (c)(1),
(2), (4) Date: Aug. 1, 2007

(87) PCT Pub. No.: WO2006/083983
PCT Pub. Date: Aug. 10, 2006

(65) Prior Publication Data
US 2008/0161542 A1    Jul. 3, 2008

(30) Foreign Application Priority Data
Feb. 2, 2005    (EP) ..................................... 05075259

(51) Int. Cl.
A61K 51/00    (2006.01)
A61M 36/14    (2006.01)

(52) U.S. Cl. ...................... 424/1.89; 424/1.11; 424/1.65; 424/1.81; 424/1.85; 424/9.1; 544/1; 544/224

(58) Field of Classification Search .................. 424/1.11, 424/1.49, 165, 1.73, 1.81, 1.85, 1.89, 9.1; 534/7, 10–16; 544/1, 224
See application file for complete search history.

(56) References Cited

U.S. PATENT DOCUMENTS
5,714,342 A    2/1998    Komoriya et al.

FOREIGN PATENT DOCUMENTS
| WO | WO 95/24218 | 9/1995 |
| WO | WO 00/43110 | 7/2000 |
| WO | WO 01/34586 | 5/2001 |

OTHER PUBLICATIONS

Samnick et al., "Electrophysiological Study, Biodistribution in Mice . . . ", Nuclear Medicine & Biology, 1998, vol. 25, pp. 323-330.
Hackenberger, et al., "General Synthesis of Unsymmetrical Norborname Scaffolds as Inducers for Hydrogen Bond Interactions in Peptides", J. Org. Chem., 2004, 69, pp. 739-743.
Houle et al., "Imaging the 5-HT1A receptors with PET: WAY-100635 and analogues", Nuclear Medicine and biology, vol. 27, No. 5, Jul. 2000, pp. 463-466, XP004216841, p. 465, col. 1, paragraph 4.
Wilson et al., "Derivatives of way 100635 as potential imaging agents for 5-ht1a receptors: syntheses, radiosyntheses, and in vitro and in vivo evaluation—A new 5-HT1A receptor ligand", Nuclear Medicine and Biology, vol. 25, No. 8, Nov. 1998, pp. 769-776, XP004142586, p. 771; compounds 7, 8, 13.
Cliffe, "A retrospect on the discovery of way-100635 and the prospect for improved 5-HT1A receptor PET radioligands", Nuclear Medicine and Biology, vol. 27, No. 5, Jul. 2000, pp. 441-447, XP004216838, abstract, figures 5-5; compounds 9, 13.
Zhuang, et al., "Synthesis and evaluation of 4-(2'-Methoxyphenyl)-1-02'-UN-2-Pyridinyl)-P-Iodobenzamidoethylpiperazine (P-MPPI): A new iodinated 5-HT1A Ligand", Journal of Medicinal chemistry, American Chemical Society, vol. 37, No. 10, May 13, 1994, pp. 1406-1407, XP002027735, p. 1406: figure 1, p. 1407, col. 2, paragraph 1.
Lang et al., "Development of fluorine-18-labeled 5-HT1A antagonists" Journal of Medicinal Chemistry, May 6, 1999, vol. 42, No. 9, pp. 1576-1586, XP002421051, p. 1578; figure 1; compounds 4B, 4C.
Lang et al., "Fluoro analogs of WAY-100635 with varying pharmacokinetics properties", Nuclear Medicine and Biology, vol. 27, No. 5, Jul. 2000, pp. 457-462, XP004216840, abstract; p. 458, col. 1; figure 1.
Zhuang et al., "Isoindol-1-one analogures of 4-(2'-methoxyphenyl)1-[2'[N-(2' '-pyridyl)-p-iodobenzamido]ethyl]piperazine (p-MPPI) as 5-HT1A receptor ligands", Journal of Medicinal Chemistry, American chemical Society, vol. 41, No. 2, Jan. 15, 1998, pp. 157-166, XP002357875, abstract.
Abou-Gharbia et al., "Synthesis and Sar of Adatanserin: Novel Adamantyl Aryland Heteroarylipiperazines With Dual Serotonin 5-HT1A and 5-HT2 Activity as Potential Anxiolytic and Antidepressant Agents", Journal of Medicinal Chemistry, American chemical Society, vol. 42, No. 25, 1999, pp. 5077-5094, XP000973607, p. 5078-p. 5079; figure 1.
Raghupathi et al., "Analogues of the 5-HT1A Serotonin antagonist 1-(2-Methoxyphenyl)-4-4-(2-Phthalimido) But Ylpiperazine with Reduced Alpha1-Adrenergic Affinity", Journal of Medicinal Chemistry, American chemical Society, vol. 34, No. 8, 1991, pp. 2633-2638, XP000986140, compound 2K.
Orjales et al., "New (2-methoxyphenyl)piperazine derivatives as 5-HT-1A receptor ligands with reduced alpha-1-adrenergic activity. Synthesis and structure-affinity relationships", Journal of Medicinal chemistry, American Chemical Society, vol. 8, No. 38, 1995, pp. 1273-1277, XP002074046, compounds 2A,2B,2C,2F,2G,2H,2I.
Braker et al., Radioiodination of bridgehead carbon atoms in adamantine structures, 2003, J. Label. Compd. Radiopharm, 46: S190, abstract.
Carson et al., "Evaluation of a new F-18 labelled analog of the 5-HT antagonist WAY-100635 for PET", J. Nucl. Med, 39,1998, p. 135, abstract 553.
Hnatowich et al., "Radioactive Labelling of Antibody: A simple and efficient method", 1983, 220, pp. 613-615.
Pelegrin et al., "Photoinnunodiagnosis with antibody-fluorescein conjugates: in vitro and in vivo preclinical studies", Journal of Cellular Pharmacology, 1992, 3, pp. 141-145.
Achilefu et al., "Novel receptor-targeted fluorescent contrast agents for in vivo tumor imaging", Investigative Radiology, 2000, 35(8), pp. 479-485.
Ballow et al., "Tumor labeling in vivo using cyanine-conjugated monoclonal antibodies", Cancer Immunology and Immunotherapy, 1995, 41, pp. 157-263.
Della and Tsanaktsidis, "Synthesis of bridgehead-bridgehead substituted bicycloalkanes", Aust. J. Chem, 1985, 38, pp. 1705-1718.

(Continued)

Primary Examiner — D L Jones

(57) ABSTRACT

The present invention relates to compounds having the general formula: Y-L-BFR-X wherein BFR is a bridged fused ring system; Y is a targeting group; L is optionally present and is a linker for coupling Y to BFR; and X is halogen (e.g., radiohalogen) or a functional group for labelling.

21 Claims, 10 Drawing Sheets

OTHER PUBLICATIONS

Licha et al., "New contrast agents for optical imaging: acid-cleavable conjugates of cyanine dyes and biomolecules", In Biomedical Imaging: Reporters, Dyes, and Instrumentation, Proceeding of SPIE, 1999, 3600, pp. 29-35.

Priefer et al., "Effective synthetic routes to cubylcarbionol derivatives", Synthesis, 2002, pp. 2671-2673.

Eaton, Phillip. E., Cubanes: Starting Materials for the Chemistry of the 1990s and the New Century, Agnew. Chem. Int. Ed. Engl., 1992, 31, 1421-1436.

Braker et al., Adsorption of radioiodine on platinum: a fast and simple column method to obtain concentrated and pure radioiodide in either water or anhydrous solvents, Appl. Radiat. Isot., 2002, 57, pp. 475-482.

Della and Tsankatsidis, "Synthesis of bridgehead-bridgehead substituted biocycloalkanes", Aust. J. Chem., 1985, 38, pp. 1705-1718.

Priefer, et al., Effective Synthetic Routes to Cubylcarbinol Derivatives, Synthesis, 2002, pp. 2671-2673.

Bunce, "A mercury salt pathway for the degradation of carboxylic acids to alkyl halides suing halogen and mercuric oxide", J. Org. Chem., 1972, 37, pp. 664-669.

Herscheid et al., "Synthesis of 123I-Radiopharmaceuticals with the Label in a Bridgehead Position", 2005, J. Label. Compd. Radiopharm, 48: S54 abstract.

X = I*, F* or CH$_2$F*

NT₁/NT₂ receptor

P-glycoprotein pump

NMDA receptor

5HT₃/5HT₄ receptor

Scheme 1

BRIDGEHEAD LABELLED COMPOUNDS AND METHODS OF USING THE SAME

CROSS-REFERENCE TO RELATED APPLICATIONS

This application is a U.S. national stage application of PCT/US2006/003600, filed Jan. 30, 2006, which in turn claims priority to European patent application No. 05075259.1, filed Feb. 2, 2005.

The present invention relates to chemically labelled compounds and to the use of such compounds in diagnosis and therapy.

Today, diagnosis of a patient is rarely done without the use of imaging technology. One of the goals of imaging is to reduce the need for invasive methods. It is not only more comfortable and safe to the patient, but imaging allows views of anatomy and physiology that may not be obtained by other means.

In general, imaging can address two issues: structure and function. One can either view structures in the body and image anatomy or view chemical processes and image biochemistry. Structural imaging techniques include x-rays, CT (Computerized Tomography) and MRI (Magnetic Resonance Imaging). It is currently the role of SPECT (Single Photon Emission Computed Tomography) and PET (Positron Emission Tomography) imaging to enable viewing of biochemical processes inside the body.

PET and SPECT are imaging techniques in which a radionuclide is synthetically introduced into a molecule of potential biological relevance, also designated as a tracer, and administered to a patient. Depending on the nature of the so-called radiopharmaceutical, it may be administered in any of a number of appropriate manners such as, for example, by inhalation, ingestion or, most commonly, intravenous injection. The subsequent uptake of a radiotracer is measured over time and used to obtain information about the physiological process of interest. Because of the high-energy (gamma-ray) emissions of the specific isotopes employed and the sensitivity and sophistication of the instruments used to detect them, the two-dimensional distribution of radioactivity within a slice may be inferred from outside of the body. Thus, PET and SPECT are both emission and tomographic (from the Greek tomos for cut) techniques. Both features distinguish these modern imaging modalities from more conventional radiographic methods, like a chest x-ray, where an external source of radiation is transmitted through the subject to create a planar silhouette of the body's organs and cavities. Whereas PET and SPECT rely on similar principles to produce their images, important differences in instrumentation, radiochemistry, and experimental applications are dictated by inherent differences in their respective physics of photon emission.

Unstable nuclides that possess an excess number of protons may take one of two approaches in an effort to reduce their net nuclear positively. In one radioactive decay scheme, a proton is converted to a neutron and a particle called a positron (denoted epsilon+ or beta+) is emitted. Of identical mass but opposite charge, positrons are the antimatter equivalent of electrons. When ejected from the nucleus, a positron collides with an electron, resulting in the annihilation of both particles and the release of energy. The principles of conservation of mass and momentum dictate that two photons (gamma-rays) are produced, each of equivalent energy and exactly opposite trajectory (180° apart). For this reason, PET is sometimes referred to as dual photon emission tomography. Among the most commonly used positron-emitting nuclides in PET procedures are 11-carbon ($^{11}$C), 13-nitrogen ($^{13}$N), 15-oxygen ($^{15}$O), and 18-fluorine ($^{18}$F).

The unique spatial signature of back-to-back photon paths is exploited by PET scanners in locating the source of an annihilation event, a method known as coincidence detection. A PET scanner may be conceptualized as a ring like camera that surrounds the body. Instead of using photographic film, however, PET (and SPECT) scanners employ highly sensitive scintillation detectors made of dense crystalline materials (e.g., bismuth germanium oxide, sodium iodide, or cesium fluoride), which capture the invisible, high-energy gamma-rays and convert them to visible light. This brief flash of light is converted into an electrical pulse by an immediately adjacent photomultiplier tube (PMT). The crystal and PMT together make up a radiation detector. Rather than using individual detectors in isolation, a PET camera is constructed such that opposing detectors are electronically connected. When separate scintillation events in paired detectors coincide, an annihilation event is presumed to have occurred at some point along an imaginary line between the two. This information is registered by a computer and later used to reconstruct images using the principles of computed tomography. Conversely, single events are ignored. Although it is conceivable that two unrelated photons from spatially separate annihilation events might reach opposing detectors in unison, these accidental coincidences are much less frequent than true ones. In fact, coincidence detection is a very efficient technique and contributes to PET's superior sampling rates and sensitivity.

One intrinsic limitation of PET derives from the nature of positron decay and the principle of coincidence detection. Specifically, PET recognizes the site of positron annihilation and not the site of radioactive decay. Since a positron must generally come to rest in tissues before being able to collide with an electron, annihilation often occurs some distance away from the positron's origin. The distance separating these two events, decay and annihilation, depends on the average kinetic energy of the positron as it leaves the nucleus, and varies according to the specific isotope involved. For $^{11}$C decay, this range is roughly 2 mm. In addition, if the positron is not entirely at rest at annihilation, photons will be emitted at an angle slightly different than 180°. Taken together, remote positron annihilation and photon noncolinearity place a theoretical limit on PET's achievable spatial resolution, which is estimated at 2-3 mm.

In an alternative scheme to positron emission, certain proton-rich radionuclides may instead capture an orbiting electron, once again transforming a proton to a neutron. The resulting daughter nucleus often remains residually excited. This metastable arrangement subsequently dissipates, thereby achieving a ground state and producing a single gamma photon in the process. Isotopes that decay by electron capture and/or gamma emission are used in SPECT, and include both 123-iodine ($^{123}$I, e.g., brain applications), the long-lived metastable nuclide 99m-technetium ($^{99}$mTc, e.g., bone, liver and brain applications) and Ga-67 (e.g., various tumor applications). Because gamma-rays are emitted directly from the site of decay, no comparable theoretical limit on spatial resolution exists for SPECT. However, the emission of a single photon means that instrumentation in SPECT must be intrinsically different from that in PET. Instead of coincidence detection, SPECT utilizes a technique known as collimation. A collimator may be thought of as a lead block containing many tiny holes that is interposed between the subject and the radiation detector. The holes are sufficiently long and narrow so as to permit only photons of essentially parallel trajectory to pass through the collimator and reach the detector. Given knowledge of the orientation of a collimator's holes, the original path of a detected photon is linearly extrapolated. In contrast to parallel photons, gamma-rays, which deviate slightly are absorbed by the lead and go undetected. As might be imagined, collimation is less efficient than coincidence detection, because many potentially informative photons are filtered out. Although collimation is less sensitive than PET, advances in collimator design and radiation detection have made SPECT sufficiently sensitive for routine use in nearly all of the same applications.

Although the physical principles relating to photon emission and detection are different, the means by which PET and SPECT translate information about photon paths into cross-sectional body images are largely the same. Because only information about a photon's direction, not depth, is known, views of photon trajectories from multiple angles around the entire head are required. A set of measurements from a given angle or viewpoint is referred to as a projection. In PET, multiple projections are obtained by a ring of essentially contiguous radiation detectors, whereas SPECT cameras typically use several detector heads that rotate around the subject in synchrony and collect data over an entire 360°. After recording many thousands of trajectories from multiple projections, a picture of the distribution of radioactivity within a given body slice is created by retracing or "back-projecting" the trajectories of gamma-rays across the field of view for every imaging angle. The method of backprojection, although complex, is conceptually analogous to the simple puzzle in which numbers in a square grid are inferred from their sums along each row. However, PET and SPECT images consist of much larger matrices (e.g., 128×128 or 256×256 elements) of radiation density values. Thus, fast computer coprocessors and efficient mathematical algorithms (fast Fourier transformations) are usually used to handle the enormous amounts of data and the intensive calculations involved. Once their radiation values are determined, individual matrix elements are assigned corresponding shades of color and displayed as picture elements or pixels on a video terminal. In this manner, a PET or SPECT image of the distribution of radioactivity within the body is produced.

Presently, the method of simple backprojection is rarely used for reconstructing images. Rather a modified technique known as filtered backprojection is nearly universally applied. The reason for filtering relates to quantitative imaging artifacts introduced by the method of backprojection itself, even in the absence of other sources of statistical noise. In retracing a photon's path, the actual point of decay is indeterminate. Thus, the backprojection algorithm is forced to assume an equal probability of radioactive decay, and hence radiation value, for every point along the line of trajectory. Areas of the body that have high concentrations of radioactivity will standout as many trajectories from multiple projections are superimposed and their probability values summed. However, areas that contain no radioactivity will bear the residual imprint of the algorithm's statistical guess, and small, but finite, values are ascribed to areas where none should exist. Although this problem decreases with increased spatial sampling and greater numbers of projections, a filter is usually still used to restore quantitative accuracy by subtracting spurious values from the images. Multiple filtering techniques have been developed, and the considerations involved in choosing one, depend on the specific application required. The skilled person can for example select a filtering technique based on the trade-offs between filters taken into account their relative impact on spatial resolution and noise amplification. Thus, filter selection can be determined by the imaging context.

Summarizing, both SPECT and PET use the idea of a "tracer", which refers to an analogue of a biologically active compound in which one of the atoms has been replaced by a radioactive substituent (e.g., radioactive atom or a molecule including a radioactive atom) to image chemical processes. When the tracer is introduced into the body, its site-specific uptake can be traced by means of photons (gamma-rays) emitted by the labelled atom.

In SPECT, the radioactive atoms of the tracers are commonly Tc-99m (e.g., bone, liver and brain applications), I-123 (e.g., brain applications) and Ga-67 (e.g., various tumour applications). In the body, when one of these radioactive atoms decays, the emitted photons are detected by the SPECT imaging apparatus. SPECT's ability to image some chemical processes is hindered by the fact that isotopes tend to be relatively large atoms that are not ideal for use in labelling some compounds due to steric reasons.

PET uses tracers labelled with positron emitting isotopes (e.g., Fluorine-18 and Carbon-11). These isotopes have a relatively short half-life, which reduces the time of exposure to the patient. In particular, Fluorine-18 exhibits a half-life of just less than about 2 hours, and Carbon-11 exhibits a half-life of only about 20 minutes. One advantage of PET is added sensitivity.

The clinical uses of PET and SPECT brain imaging can be roughly divided into measurements of local neuronal activity, neurochemistry, or in vivo pharmacology. Local neuronal activity is associated with energy consumption and can be measured with glucose metabolism which itself is usually positively coupled with blood flow. Thus, PET tracers for measurement of local neuronal activity may include [$^{18}$F] FDG (glucose metabolism) and [$^{15}$O]H$_2$O (blood flow). On the other hand, SPECT does not have a comparable tracer for glucose metabolism but may use $^{99}$mTc- and $^{123}$I-labeled compounds, as well as $^{133}$Xe to provide measures of blood flow.

The clinical uses of PET and SPECT imaging to measure local neuronal activity can be used to determine neurological disorders and include localization of both cerebral ischemia and epileptic focus and distinguishing radiation necrosis from tumor growth. In at least the latter two conditions, imaging results can directly impact clinical care. For example, the neurosurgical treatment of patients with medication refractory epilepsy critically depends upon accurate localization of the seizure focus, which is often distant from the surface of the brain and poorly localized by scalp electrode electroencephalogram (EEG). In the interictal period, the seizure focus is hypometabolic and has decreased blood flow. PET and SPECT imaging has been used either as a primary means of localization or confirmation of other diagnostic tests to select the portion of the brain that is subsequently resected. In the ictal period, the seizure focus is associated with increased metabolism and increased blood flow and may have a greater likelihood of showing positive localization than interictal imaging.

PET imaging has been elegantly combined with neuropsychological activation studies to localize cognitive functions, including reading, speaking, and word associations. The short half-life of $^{15}$O ($T_{1/2}$ of 2 min) allows multiple (often 8 to 10) bolus injections of the tracer in one experimental session. Thus, both baseline scans and those following neuropsychological tasks can be repeated and averaged.

Two major attributes of PET and SPECT, high sensitivity and chemical selectivity, make these methods particularly well suited for in vivo neurochemical measurements. The sensitivity of PET and SPECT to detect radiotracers is less than $10^{-12}$ M, which is orders of magnitude greater than the sensitivity of MRI ($10^{-3}$ to $10^{-5}$ M). In a manner exactly analogous to nonradioactive drugs, radiotracers can be developed to label specific target sites in the brain. These specific tracers can, thereby, provide measures of multiple neurochemical pathways in the brain, including synthesis and release of transmitters, receptors, reuptake sites, metabolic enzymes, and possibly even second messenger systems.

Among these receptor studies have probably received the greatest effort among the various targets of neurochemical imaging. If a receptor is selectively altered in a specific disease, then imaging of this site may provide diagnostic information about the disorder. For the DA receptor system, the Johns Hopkins PET group has reported that drug-naive schizophrenic patients have a 2.5-fold elevation of dopamine D2 receptor density in the striatum using the virtually irreversible tracer [$^{11}$C]N-methylspiperone and kinetic modeling Another example of a diagnostic application using receptors is the use of a tracer for imaging of serotonin receptor density in the brain. The serotonin (5-hydroxytryptamine, 5-HT) system is an important neurotransmission network that is involved in modulation of various physiological functions and behaviour, such as thermoregulation, cardiovascular function, aggressive and sexual behaviour, mood, appetite and the sleep-wake cycle. Serotonin is synthesized from the amino acid L-tryptophane by sequential hydroxylation and decarboxylation. It is stored in presynaptic vesicles and released from nerve terminals during neuronal firing. One of the best-characterized binding sites for serotonin is the 5-HT$_{1A}$ receptor. 5-HT$_{1A}$ receptors function as somatodendritic autoreceptors in the raphe nuclei as well as postsynaptic receptors in the terminal fields.

The 5-HT$_{1A}$ subtype of serotonin receptors has been implicated in the pathogenesis of anxiety, depression, hallucinogenic behaviour, motion sickness and eating disorders and is therefore an important target for drug therapy. Antidepressant drug treatments are believed to involve down-regulation or other adaptive changes of the central 5-HT$_{1A}$ subpopulation.

It has also been proposed that antagonists of the 5-HT$_{1A}$ receptor could ameliorate symptoms of dementia by facilitating glutamate release and thereby compensate to some extent for the loss of cortical glutamate neurons, which is thought to occur in Alzheimer's disease. A gradual loss of 5-HT$_{1A}$ receptors occurs in normal aging, whereas a much more prominent loss is apparent in the Alzheimer brain. Finally, several laboratories have reported elevated neocortical 5-HT receptor binding (including the 5-HT$_{1A}$ subtype) in schizophrenia.

Many researchers have tried to develop a radioligand capable of assessing in vivo changes in 5-HT$_{1A}$ receptors in depressed subjects, people with anxiety disorders, patients with Alzheimer's disease and schizophrenics. Non-invasive imaging techniques could provide an important opportunity to investigate the functional role of central 5-HT$_{1A}$ receptors in healthy volunteers, the relation of the 5-HT$_{1A}$ subtype to various neuropsychiatric diseases, and/or the occupancy of 5-HT$_{1A}$ receptors in the human brain by novel drugs.

Several tracers for 5-HT$_{1A}$ receptors have been prepared and evaluated for imaging purposes. Compounds with structural similarity to the 5-HT$_{1A}$ antagonist, N-[2-[4-(2-methoxyphenyl)-1-piperazinyl]ethyl]-N-(2-pyridinyl) cyclohexanecarboxamide (WAY-100635) were found to be the most promising. WAY-100635 itself has been labelled with Carbon-11 in the positions a or b (see FIG. 1).

Since the main metabolic pathway of WAY-100635 is hydrolysis of the amide bond (see FIG. 1), a label in the cyclohexanecarbonyl moiety (position b) is favoured. If not, the lipophilic metabolite (WAY-100634) carries the label, and, as this compound also enters the brain and binds to other receptors ($\alpha$1 and non-specific), it interferes with the tomographic measurements. However, when the carbon-11 label is to be part of the cyclohexyl moiety, the synthesis will be more complex. An approach to simplify the methylation procedure is to prevent the compound from amide hydrolysis using more bulky groups (see FIG. 2) instead of the cyclohexanecarbonyl, like in CPC-222 or Wilson-8 (A A Wilson et al. (1998) *Derivatives of WAY 100635 as potential imaging agents for 5-HT$_{1A}$ receptors: syntheses, radiosyntheses, and in vitro and in vivo evaluation*, Nucl. Med. Biol. 25, 769-776). Although these compounds have a comparable affinity with regard to WAY-100635, and have been shown to be stable towards hydrolysis, the short physical half-life of Carbon-11 still prevents the use of these compounds in hospitals that do not have their own production facility (e.g., a cyclotron and a GMP compliant radiochemistry laboratory).

A longer lived isotope will allow transportation over a long distance and may also have an advantage in giving better count statistics in the final stage of a scan and in accompanying analysis of radioactive metabolites in plasma.

Thus research has been directed towards derivatives of WAY-100635 labelled with Fluorine-18 ($t_{1/2}$=110 min) or Iodine-123 ($t_{1/2}$=13.2 hours) (see FIG. 3). However, for WAY derivatives MPPF and MPPI, containing an aromatic moiety in the carboxamide part, the calculated binding potentials were found to be 4-6 times lower than those for WAY-100635. In addition, these compounds showed a lower selectivity due to a quite high affinity for the $\alpha$1-adrenoceptors, whereas they were also rapidly metabolized.

Using a saturated moiety (FCWAY, see FIG. 3) this problem has been overcome, but elimination of H$^{18}$F from the cyclohexane ring leads to a substantial skull uptake of [$^{18}$F] amounting to twice the whole brain average at 60 min, which seriously hampers clinical application (Carson et al. (1998) *Evaluation of a new F-18 labelled analog of the 5-HT$_{1A}$ antagonist WAY-100635 for PET*, J. Nucl. Med. 39, 135P, abstract 553). Therefore, the search for novel fluorinated ligands is still an ongoing challenge.

An at least generally similar problem exists with regard to iodinated ligands for SPECT. At this time, SPECT cameras are more widely distributed over hospitals than PET cameras, which are only present in a few centres. However, a major drawback is that aliphatic iodinated compounds are inherently instable in vivo, which is caused by the fact that they are easily susceptible to nucleophilic substitution and elimination. Therefore, in radiopharmaceuticals, iodine is until now always attached to an sp$^2$ carbon atom in either an aromatic or a vinylic moiety. As can be seen from MPPI (FIG. 3), this often reduces the binding affinity.

Figure 1:
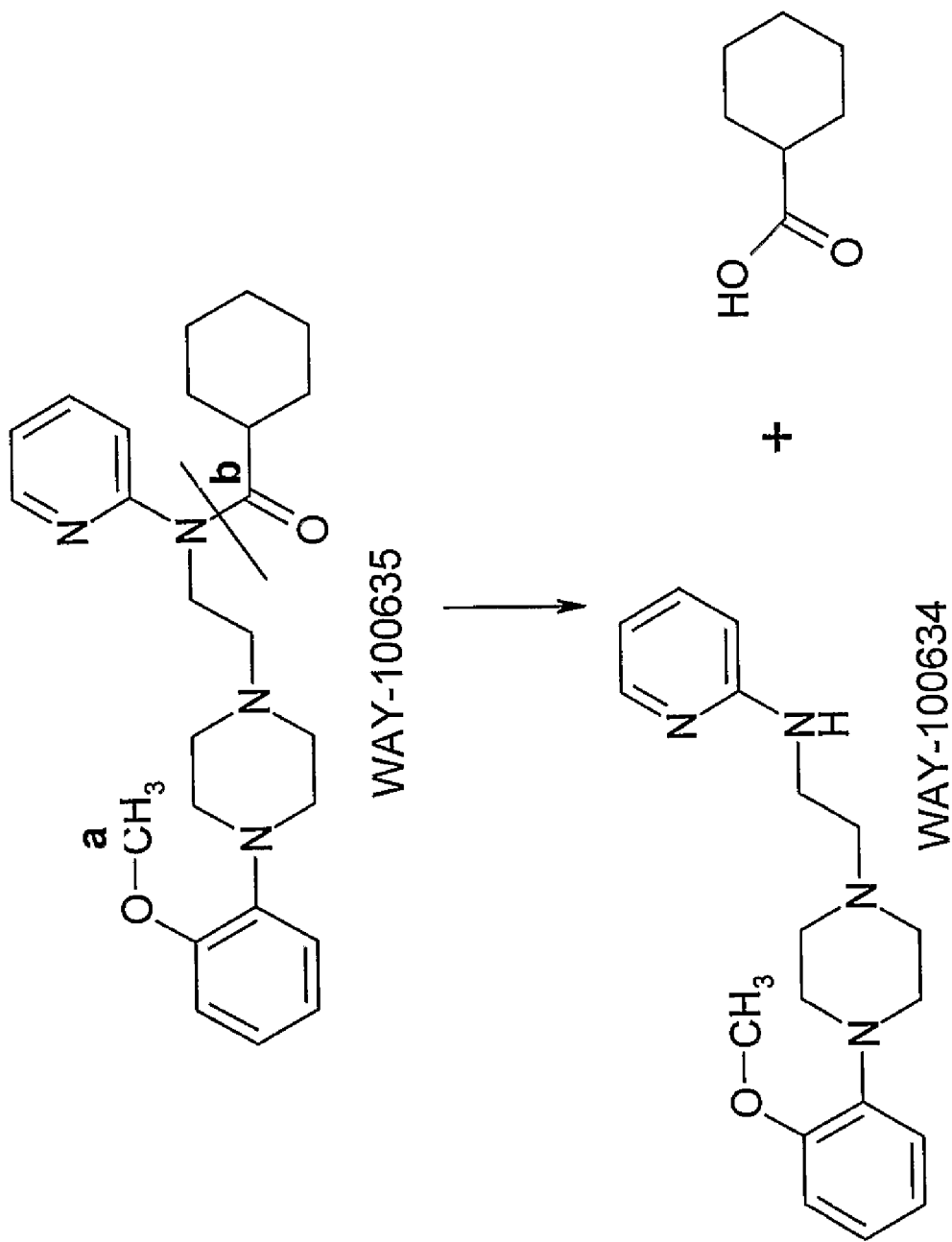
FIG. 1 shows hydrolysis of the amide bond of WAY-100635, which is the main metabolic pathway for that compound.
Figure 2:
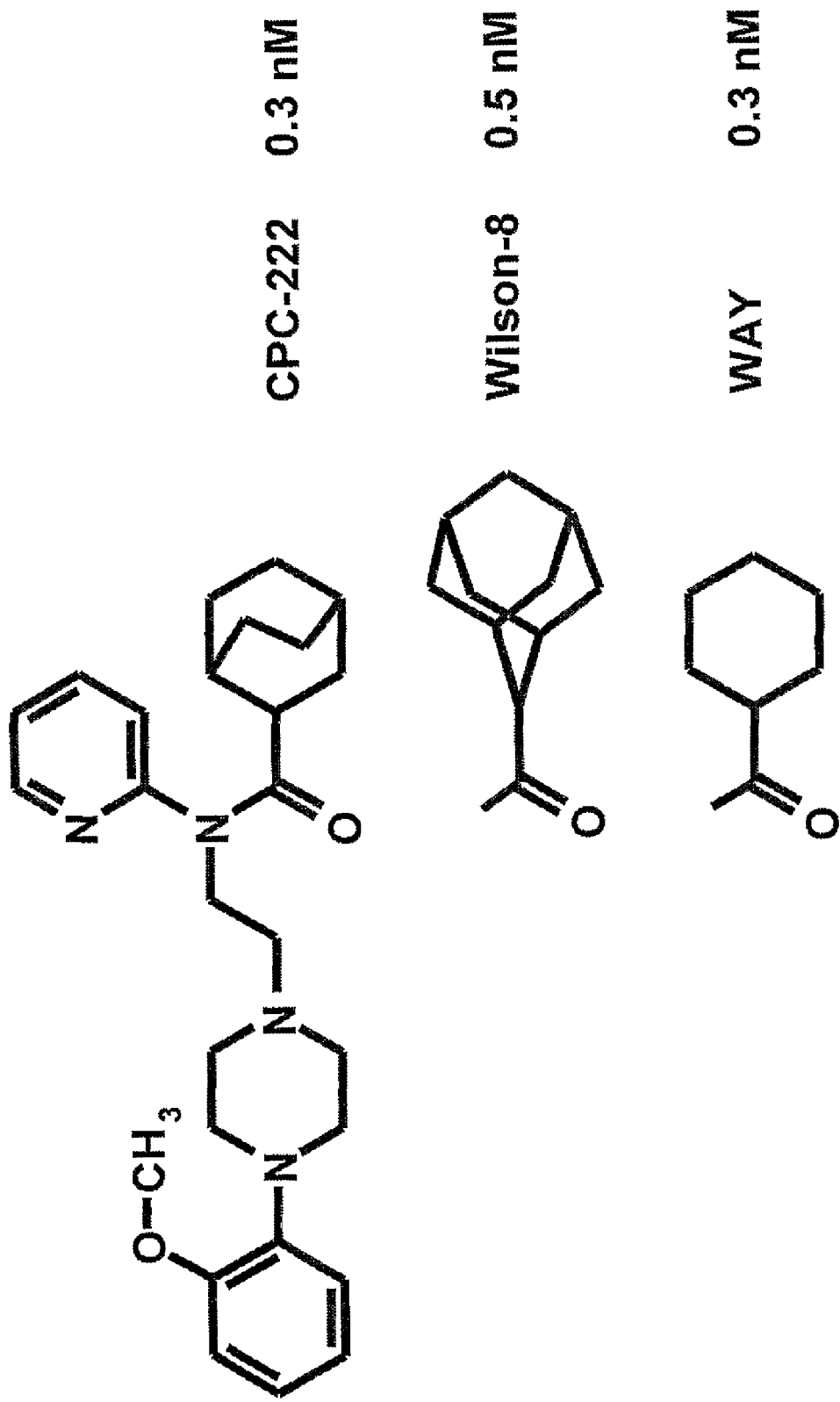
FIG. 2 illustrates some exemplary bulky groups that may be substituted for the cyclohexanecarbonyl in WAY derivatives to prevent amide hydrolysis.

In the research that led to the present invention, new chemically labelled, biologically active compounds were developed. For instance, a first aspect of the invention relates to compounds having the general formula:

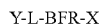

wherein BFR is a bridged fused ring system, which is optionally substituted; Y is a targeting group (sometimes referred to herein as a "biologically active compound"); L is optionally present and is a linker for coupling Y to BFR; and X is a halogen (e.g., radioactive halogen), a $CH_2F$ functionality that is optionally radioactive, or a leaving group. The term "leaving group" as used herein refers to a group displaced by an incoming nucleophile. Particularly suitable leaving groups are weak bases such as the anionic groups —OH$^-$, —NH$_2^-$, —F$^{-1}$, —Cl$^-$, —Br$^-$, —I$^-$, and -TosO$^-$.

In some particularly preferred embodiments of this first aspect of the invention, X is coupled to a bridgehead (e.g., bridgehead carbon atom) of BFR. Incidentally, a "bridgehead atom" (also referred to herein as a "bridgehead") is any skeletal atom of a ring system, which is bonded to three or more skeletal atoms (excluding hydrogen).

The targeting group (Y) may be any moiety capable of directing X to the desired site to be diagnosed or treated such as an organ or tissue. In some embodiments, the targeting group may refer to or be associated with biomolecules including proteins, peptides, enzymes, antibodies and fragments thereof, amino acids, peptidomimetics, nucleic acids, RNA, DNA, nucleosides, nucleotides, carbohydrates, glycomimetics, lipids, phospholipids, hormones, metabolic compounds, signal molecules, neurotransmitters, vitamins and analogues or derivatives thereof. In some embodiments, the targeting group may refer to or be associated with a synthetic molecule such as a polymer or a small molecule.

Specific examples of suitable targeting groups include: EGF for targeting the EGF receptor, glucose for targeting metabolic active sites such as tumors, FDOPA for targeting the FDOPA receptor, anti-B-FN antibody for targeting neovascular tissue, anti-CD20 antibody for targeting tumor tissue, folate for targeting the folate receptor, sialyl Lewis receptor for targeting inflammation sites, steroid hormones for targeting breast and prostate lesions; whole or fragmented somatostatin, bombesin, and neurotensin receptor binding molecules for targeting neuroendocrine tumors; whole or fragmented cholecystekinin (CCK) receptor binding molecules for targeting lung cancer; whole or fragmented heat sensitive bacterioendotoxin (ST) receptor and carcinoembryonic antigen (CEA) binding molecules for targeting colorectal cancer; dihydroxyindolecarboxylic acid and other melanin producing biosynthetic intermediates for melanoma; whole or fragmented integrin receptor and atherosclerotic plaque binding molecules for targeting vascular diseases; and whole or fragmented amyloid plaque binding molecules for targeting brain lesions.

Examples of synthetic polymers for targeting groups include polyaminoacids, polyols, polyamines, polyacids, oligonucleotides, aborols, dendrimers and aptamers.

Coupling of diagnostic and radiotherapeutic agents to biomolecules can be accomplished by methods well known in the art as disclosed in Hnatowich et al., Radioactive Labeling of Antibody: A simple and efficient method. Science, 1983, 220, 613-615; A. Pelegrin et al., Photoimmunodiagnosis with antibody-fluorescein conjugates: in vitro and in vivo preclinical studies. Journal of Cellular Pharmacology, 1992, 3, 141-145; and U.S. Pat. No. 5,714,342.

For example, aryl or alkyl activated carboxylic acids can be reacted with nucleophilic groups such as primary or secondary amines. Such activated esters include, for example, N-hydroxysuccinimide esters, sulfo-N-hydroxysuccinimide esters, and phenolic esters (e.g., phenol, p-nitrophenol, tetrafluorophenol). Other amine reactive groups include aryl and alkyl imidates and alkyl or aryl isocyanates or isothiocyanates. Sulfhydryl groups on the biomolecule can be reacted with maleimides or alpha-haloamide functional groups. Biomolecules containing naturally occurring or synthetically produced (e.g. by conjugation or from oxidized sugar moieties) aldehydes and ketones can be reacted with aryl or alkyl hydrazines, aryl or alkyl acylhydrazines, alkyl or aryl hydroxylamines.

Successful specific targeting of tracers to tumors using antibodies and peptides for diagnostic imaging of tumors has been demonstrated by us and others, for example, in S. A. Achilefu et al., Novel receptor-targeted fluorescent contrast agents for in vivo tumor imaging, Investigative Radiology, 2000, 35(8), 479-485; B. Ballou et al., Tumor labeling in vivo using cyanine-conjugated monoclonal antibodies. Cancer Immunology and Immunotherapy, 1995, 41, 257-263; and K. Licha et al., New contrast agents for optical imaging: acid-cleavable conjugates of cyanine dyes with biomolecules. In Biomedical Imaging: Reporters, Dyes, and Instrumentation, D. J. Bornhop, C. Contag, and E. M. Sevick-Muraca (Eds.), Proceedings of SPIE, 1999, 3600, 29-35.

Figure 4:
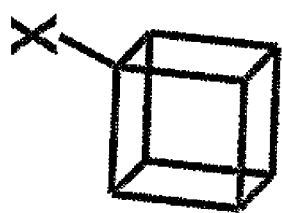
FIG. 4 illustrates the coupling of labeling group X to a bridgehead of the bridge fused ring system (BFR).
Figure 4:
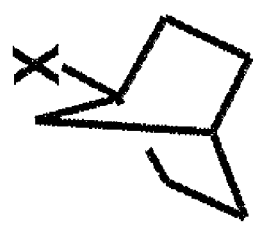
Figure 4:
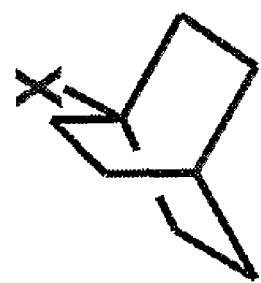
Figure 4:
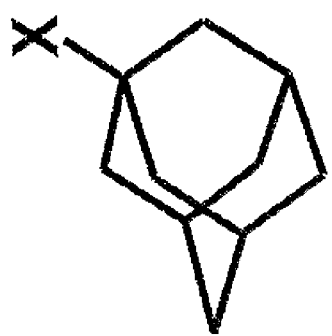

As noted above, X may be coupled to a bridgehead of the bridged fused ring system (BFR). By putting X on the bridgehead (e.g., FIG. 4), compounds may be obtained that have a slow metabolism and a stable carbon-radioisotope binding; $S_N2$ substitution is now no longer possible, whereas elimination is prevented since that leads to a highly strained system. Formation of cations is also rather difficult as can be deducted from Table 1 below (PE Eaton (1992) *Cubane: Ausgangsverbindungen für die Chemie dei neunziger Jahre und des nächsten Jahrhunderts* Angew. Chem. 1447-1462), so hydrolysis is also unlikely.

Principles of the invention can be used for labelling any biologically active compound that can be coupled, either directly or through a leaving group, to a bridged fused ring system. In this application, WAY-derivatives are described as examples of such biologically active compounds; however, it should be noted that the teachings of the present invention are applicable to a wide range of other biologically active compounds.

Y can be coupled directly to BFR or by using a linker L. In some embodiments, L may be —O(CO)—, —NH(CO)—, —NH—, —O(CH$_2$)$_n$—, —NH(CH$_2$)$_n$—, —NH(CO)NH— or —NH(CS)NH—.

The bridged fused ring system (BFR) can be a bridged fused ring system of only carbon atoms or a bridged fused ring system in which at least one carbon atom has been replaced by a heteroatom (e.g., —O—, —N—, —S—, —Se—). BFR may have a variety of substituents on the atoms not being the bridgehead; such substitution is well within the knowledge of the person skilled in the art. For instance, in some embodiments, BFR may be adamantane, bicyclooctane, norbornane or cubane. In some embodiments, BFR may be bicyclooctane, norbornane or cubane. In some embodiments, BFR is cubane.

The labelling (using X) of compounds of the invention may be accomplished using a radioactive halogen (i.e., radiohalogen). For instance, in some embodiments, the radioactive halogen is $^{18}F$, $^{123/124/131}I$, $^{76/77/82}Br$ or $^{211}At$. When X is a leaving group for labelling, it may be any appropriate leaving group. For instance, in some embodiments, X is a leaving group selected from —OH, —OSO$_2$R, —Br, —I, —Sn(alkyl)$_3$, —Pb(alkyl)$_3$, and —CH$_2$OSO$_2$R (as a precursor for —CH$_2$$^{18}$F); in which R is suitably chosen from —CH$_3$, —CF$_3$, —(C$_6$H$_4$)CH$_3$, and —(C$_6$H$_4$)NO$_2$.

Figure 5:
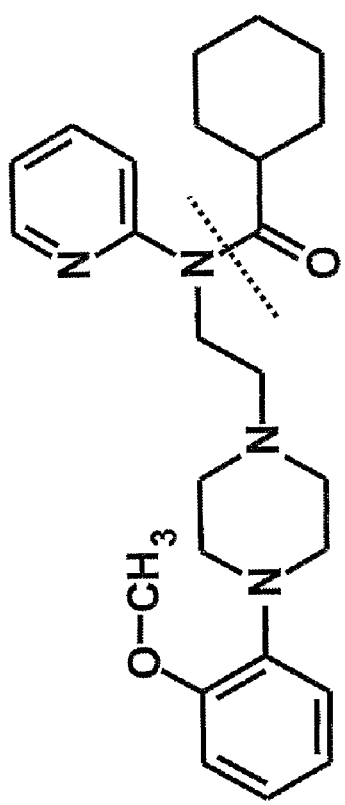
FIG. 5 shows an exemplary group of compounds that are WAY-100635 derivatives in which the cyclohexyl group is replaced by a bridged fused ring system.
Figure 5:
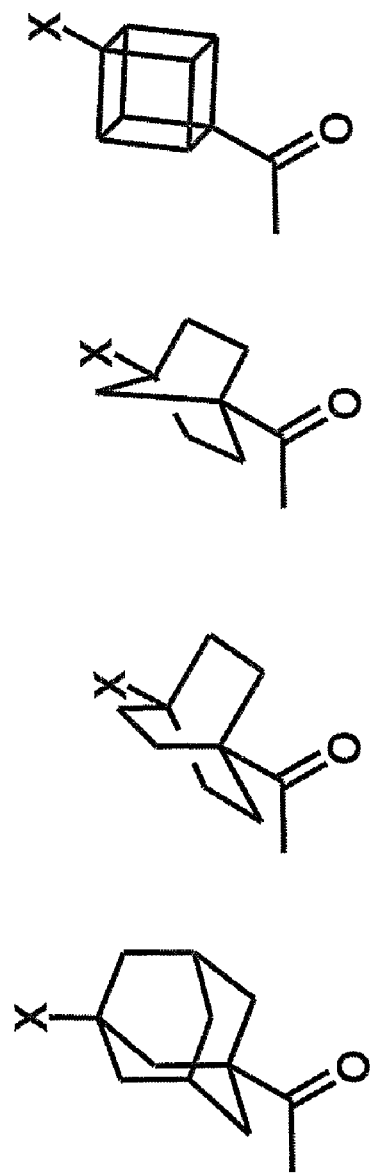

One exemplary compound of the invention is a derivative of WAY100635 in which the cyclohexyl group is replaced by a bulky structure, in particular a bridged fused ring system as shown in FIG. 5. In a particularly advantageous embodiment, the bridged fused ring system is cubane. An advantage of having not only X but also the targeting group Y such as N-(2-(4-(2-methoxyphenyl)piperazin-1-yl)ethyl)pyridin-2-amine (WAY100634) directly or indirectly coupled to a bridgehead is that the resultant radiopharmaceuticals have a symmetry element, and thus (as is the case with the use of cubane) the addition of extra chiral centers may be avoided.

Figure 10:
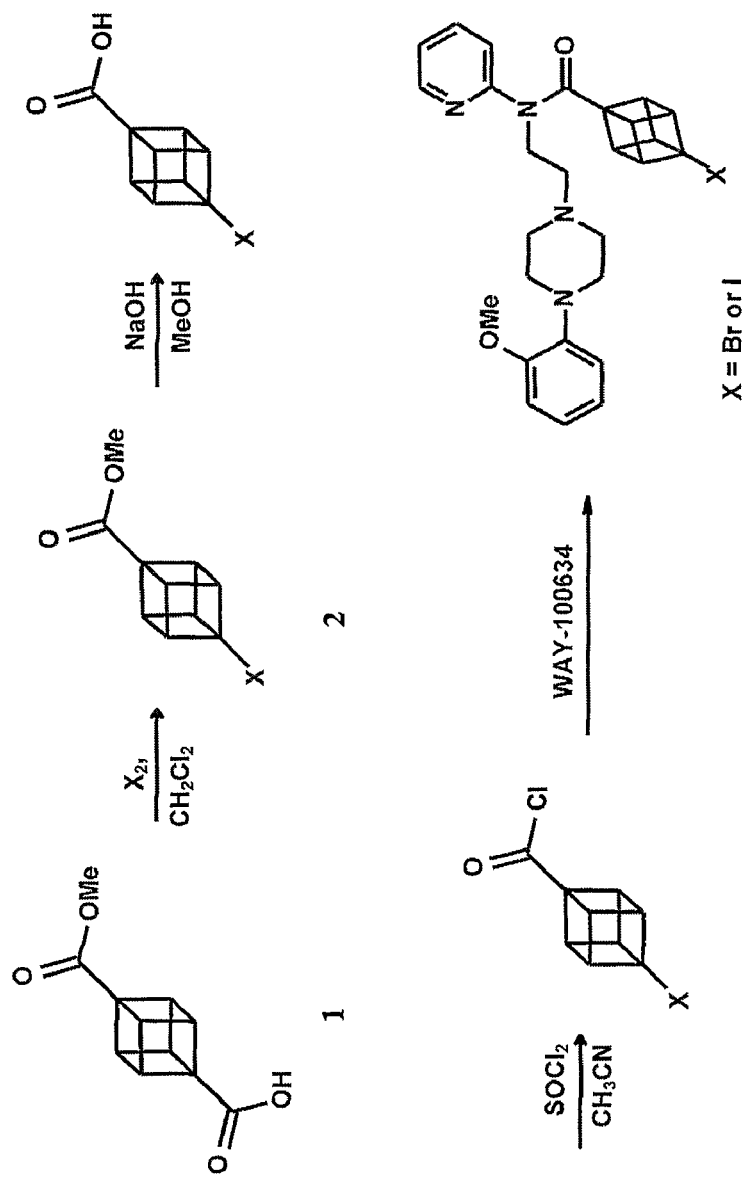
FIG. 10 shows an exemplary process for the synthesis of the compounds described herein.

An exemplary process for synthesizing compounds of the invention is shown in Scheme 1 (FIG. 10). While cubane is the illustrated bridged fused ring system, it should be noted that cubane can be replaced by other bridged structures in other embodiments of the process. As shown, bromo- or iodo-decarboxylation results in a bridgehead halogenated compound. Saponification, preparation of the acylchloride, and coupling to the pharmaceutical (WAY-100634 in the Example of the figure) is straightforward and may be accomplished in a manner known to those of ordinary skill in the art.

Figure 6:
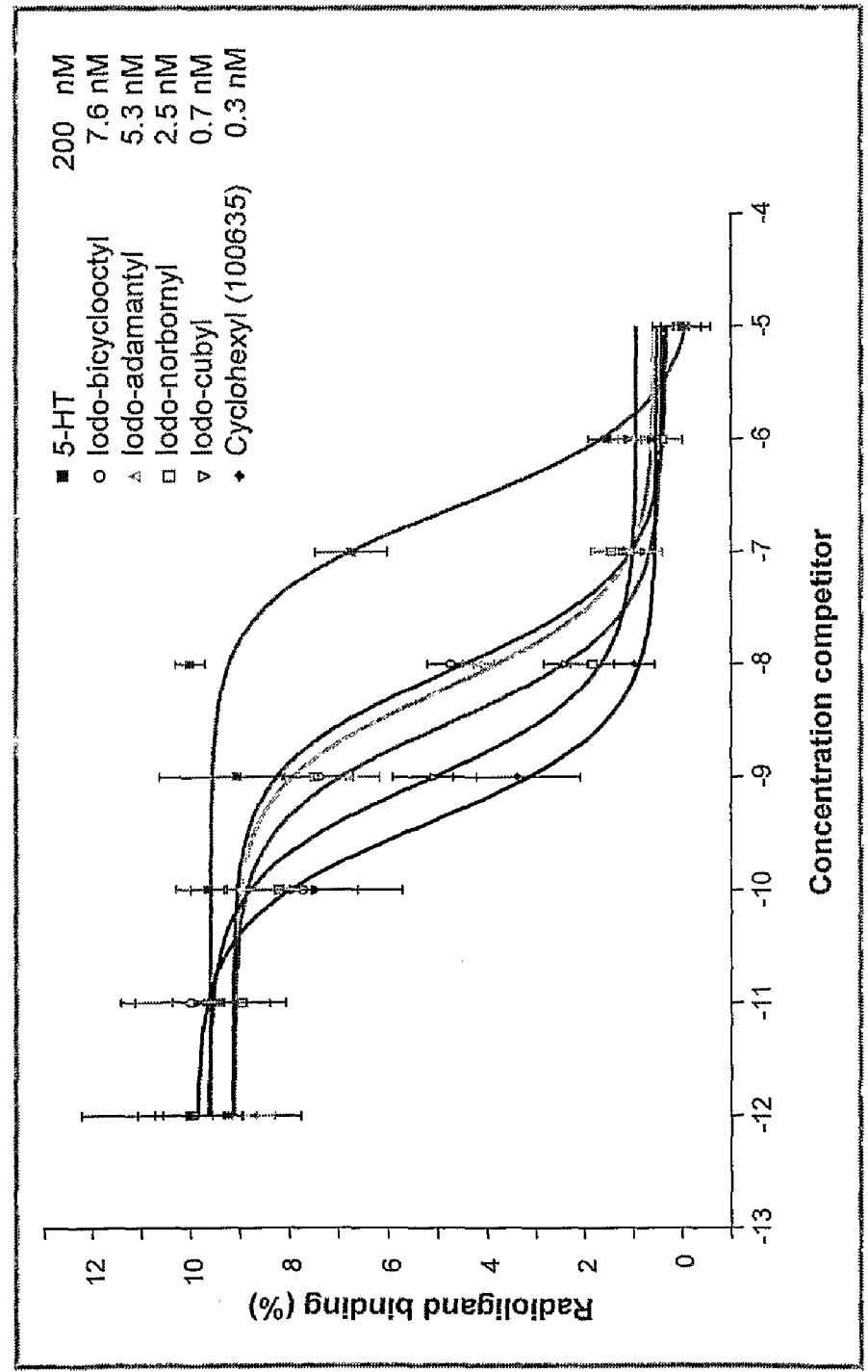
FIG. 6 shows the in vitro activity of several WAY-derivatives.

When tested for their affinity towards the human 5-HT$_{1A}$ (EXAMPLE 5), of the compounds having iodobicyclooctyl, iodoadamantyl, iodonorbornyl and iodocubyl as the BFR-X moiety, the highest affinity was found for iodocubyl-WAY, which is still in the subnanomolar range (see FIG. 6).

It was found that in both the isotopic ($^{123}$I for I) and the non-isotopic ($^{123}$I for Br) exchange, the labelling yield for tracers including cubane was significantly and surprising higher than those tracers including other bridged fused ring structures. For instance, Table 2 below, summarizing the experimental results obtained with the labelling experiment described in Example 2, shows that the yield of an iodocubane derivative (4) was surprisingly high (relative to the other derivatives) under water-free conditions using copper-two-triflate as a catalyst. This surprising result (i.e., the labelling yield for tracers including cubane) was also found for an antibody based tracer (example 7, yield 83%) and labelling of the compound (4-Bromocubane-1-yl)-acetonitrile (example 8, yield 98%).

Figure 7:
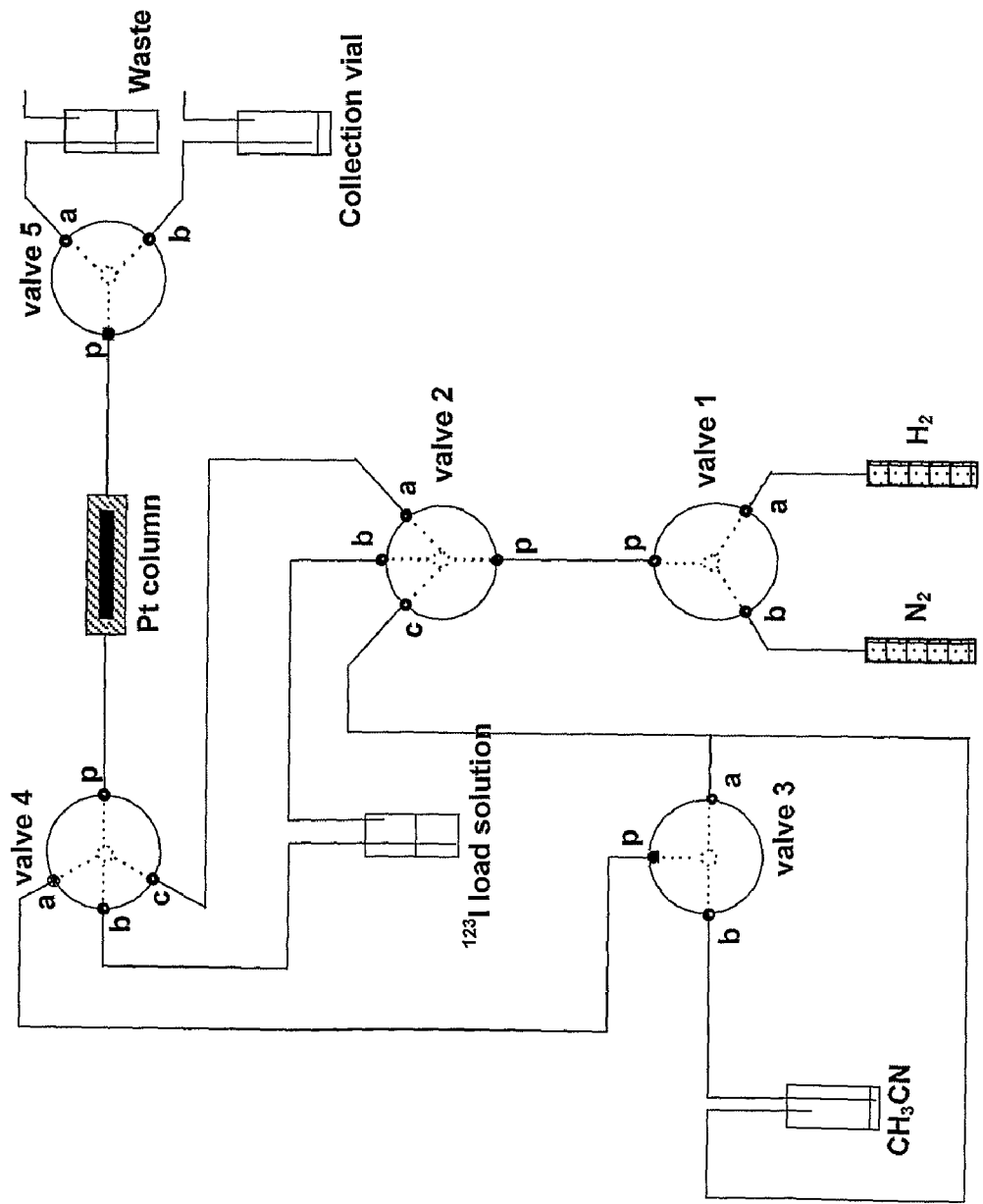
FIG. 7 shows a schematic diagram for a water-free system for purification and concentration of radioiodide.

FIG. 7 shows how a water-free solution is obtained (A H Braker et al. (2002) *Adsorption of radioiodine on platinum: a fast and simple column method to obtain concentrated and pure radioiodide in either water or anhydrous solvents* Appl. Radiat. Isot. 57,475-482; and J D M Herscheid, F P Moet *Process for the purification and concentration of radioiodide isotopes* PCT/US00/01824). In short, the target harvest-solution is acidified and iodine-123 is trapped on a platinum-filled mini-column. Water is removed by rinsing with acetone, after which the radio-iodine can be recovered in a small volume by a pulsed elution with eluant (in this case, acetonitrile) and hydrogen.

The bridgehead labelled iodine compounds were found to be very stable. They were kept in solution for more than six months without decomposition. There was no thyroid uptake observed in vivo indicating that no free iodide was formed. This absence of de-iodination was further confirmed by stability tests using human hepatocytes (see EXAMPLE 4).

A second aspect of the invention relates to labelling compounds including bridged fused ring systems. These compounds can be used for labelling targeting molecules to provide novel pharmaceuticals (e.g., radiopharmaceuticals such as tracers). The compounds of this second aspect of the invention are characterized by the general formula M-BFR-X, wherein BFR and X are as described above, and M is a leaving group that is either directly coupled to BFR or indirectly coupled to BFR by a suitable linker. In some embodiments, M can be a weak base such as, for example, an anionic group selected from the group consisting of —OH$^-$, —NH$_2$$^-$, —F$^-$, —Cl$^-$, —Br$^-$, —I$^-$, -TosO$^-$, —OSO$_2$R, —Sn(alkyl)$_3$, —Pb(alkyl)$_3$, and —CH$_2$OSO$_2$R, wherein R may be selected from the group consisting of —CH$_3$, —CF$_3$, —(C$_6$H$_4$)CH$_3$, —(C$_6$H$_4$)NO$_2$, carboxylic acids, primary and secondary amines capable of providing or being an activated ester group such as N-hydroxysuccinimide esters, sulfo-N-hydroxysuccinimide esters, and phenolic esters (e.g., phenol, p-nitrophenol, tetrafluorophenol), amine reactive groups such as aryl and alkyl imidates and alkyl or aryl isocyanates or isothiocyanates, a sulfhydryl group, a maleimide or alpha-haloamide functional group, aryl or alkyl hydrazines, aryl or alkyl acylhydrazines, and alkyl or aryl hydroxylamines. In some embodiments of this second aspect, the linker (if present) can be a straight or branched, saturated or unsaturated, optionally substituted, aryl or alkyl group including 1 to 20 carbons. For example, in some cases, the linker of this second aspect may be represented by —(CH$_2$)$_n$—, wherein n may range from 1 to 20 (e.g., 1 to 5, 1 to 7, 1 to 10, etc.).

Resulting pharmaceuticals, e.g. monoclonal antibodies, peptides, ligands of receptors etc. that are labelled with a labelling compound of the second aspect of can be used for diagnosis or therapy. The application may depend on the radioisotope used.

The steps involved in diagnostic and therapeutic methods of the invention are at least generally known to those of ordinary skill in the art. The portion of these diagnostic and therapeutic methods that was not known prior to this disclosure is the use of one or more compounds of the invention in such diagnostic and therapeutic methods. At least in some embodiments, a difference between therapeutic methods of the invention and diagnostic methods of the invention is the particular isotope included in the compound that is administered to the patient. For example, $^{123}$I-labelled molecules may be utilized for diagnostic procedures while $^{131}$I-labelled molecules may be utilized for therapeutic procedures.

One method of performing a diagnostic procedure of the invention may include administering an effective amount of a compound having the formula Y-L-BFR-X to a patient, wherein BFR, L, Y and X are as described above with regard to the first aspect of the invention. In most cases, it is generally preferred that the compound be administered to the patient as a pharmaceutically acceptable formulation (e.g., the compound is in a biologically compatible excipient). For example, a pharmaceutically acceptable formulation of a parenteral administration may include a sterile aqueous solution or suspension of the compound. Pharmaceutically acceptable formulations of the invention may contain one or more pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of a compound according to the present invention in aqueous solution or suspension. Such enteral formulations may optionally include one more buffers, surfactants, emulsifiers, thixotropic agents, and the like. Formulations for oral administration may contain flavoring agents and other ingredients for enhancing their organoleptic qualities. Formulations for topical delivery may contain liquid or semisolid excipients to assist in the penetration of the compounds according to the present invention. Compounds of the invention may be delivered in an aerosol spray. In preferred embodiments of the diagnostic method, a compound of the invention is allowed to accumulate in an area of interest (e.g., particular tissue) before PET or SPECT imaging is performed.

Some compounds of the present invention may be used as therapeutic agents. In an exemplary therapeutic method of the invention, an effective amount of a compound having the formula Y-L-BFR-X may be administered to a patient in a manner like that described with regard to the above method of performing a diagnostic procedure. With regard to the compound used for this therapeutic method, BFR, L, Y and X are as described above with regard to the first aspect of the invention.

Compounds of the invention can be formulated into diagnostic or therapeutic compounds for enteral, parenteral, topical, aerosol, inhalation, or cutaneous administration. Topical or cutaneous delivery of compounds of the invention may include aerosol formulations, creams, gels, solutions, etc. Compounds of the invention are preferably administered in doses effective to achieve the desired diagnostic or therapeutic effect. Such doses may vary widely depending upon the particular compounds employed in the formulation, the organs or tissues to be examined, the equipment employed in the clinical procedure, the efficacy of the treatment achieved, and the like. Formulations of the invention may contain an effective amount of the compound(s), along with conventional pharmaceutical carriers and/or excipients appropriate for the type of administration contemplated. These formulations may also include one or more stabilizing agents and/or skin penetration enhancing agents.

Another aspect of the invention relates to the use of a "cold" version of compounds of the invention. In these compounds of the formula Y-L-BFR-X, X is not a radionuclide but the non-radioactive form thereof (e.g., non-radioactive I, F, Br).

Figure 9:
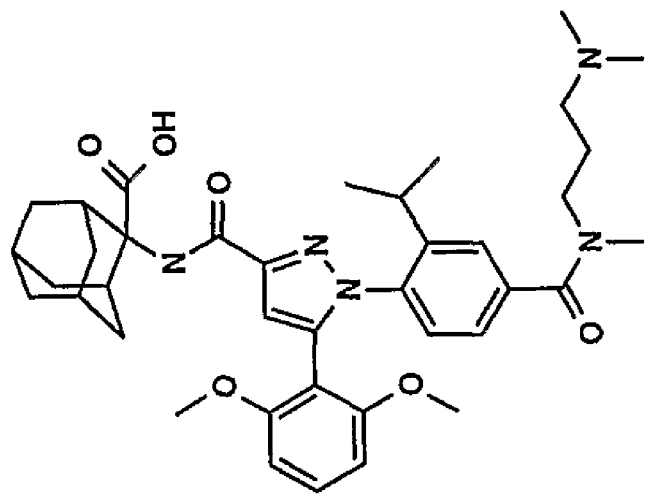
FIG. 9 shows an NMDA receptor, $5HT_3/5HT_4$ receptor, P-glycoprotein pump and $NT_1/NT_2$ receptor.
Figure 9:
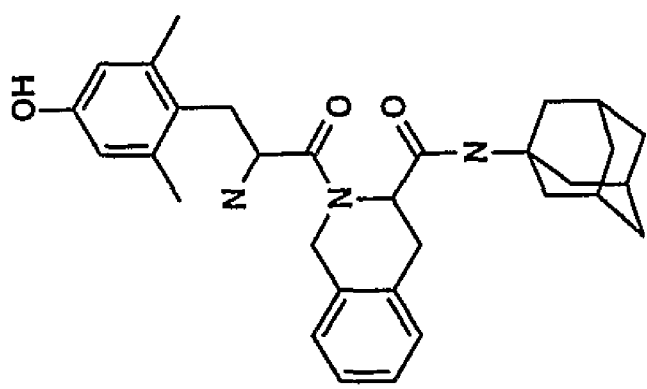
Figure 9:
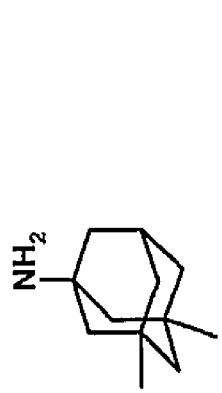
Figure 9:
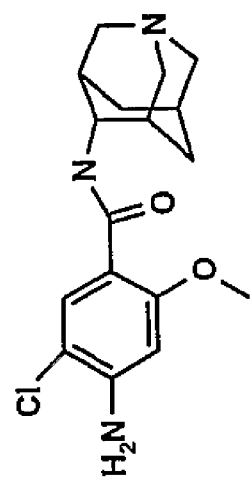

While various features of the present invention are described herein by reference to exemplary WAY-derivatives, the invention is applicable to other pharmaceuticals. Examples of pharmaceuticals that already contain a BFR are shown in FIG. 9. These compounds are known per se but have not been disclosed in labelled form.

The present invention will be further elucidated in the Examples that follow. These Examples are for illustrative purposes only and are in no way intended to limit the invention in any way.

EXAMPLE 1

Synthesis of Bridgehead Brominated and Iodinated WAY Derivatives

Synthesis of bridgehead WAY-derivatives was performed as depicted in Scheme 1 (FIG. 10).

Starting from the dimethyldicarboxylates, which are either commercial available or synthesized by literature methods (E W Della and J Tsanaktsidis (1985) *Synthesis of bridgehead-bridgehead substituted bicycloalkanes* Aust. J. Chem., 38, 1705-18), the monocarboxylic acids 1 were obtained by a controlled saponification (R Priefer et al. (2002) *Effective synthetic routes to cubylcarbinol derivatives* Synthesis, 2671-2673). Bromo- or iodo-decarboxylation using mercuryoxide (a, b, c) (N J Bunce (1972) *A mercury salt pathway for the degradation of carboxylic acids to alkyl halides using halogen and mercuric oxide* J. Org. Chem. 37, 664-669) or iodobenzene diacetate (d) (R Priefer (2002) vide supra) provided the bridgehead halogenated compounds 2.

The subsequent saponification with NaOH in methanol, preparation of the acylchlorides using $SO_2Cl_2$ and coupling to WAY-100634 was further done in using straightforward chemistry (see e.g. A A Wilson et al. (1968) *Derivatives of WAY 100635 as potential imaging agents for 5-$HT_{1A}$ receptors: syntheses, radiosyntheses, and in vitro and in vivo evaluation* Nucl. Med. Biol., 25, 769-776).

EXAMPLE 2

Preparation of Radiolabeled [$^{123}$I]iodocubane-WAY 2 mg of bromocubane-WAY precursor prepared according to Example 1 and 0.1 mg Cu(II)triflate were dissolved in 100 µl anhydrous [$^{123}$I]-iodide in acetonitrile. This mixture was heated in a closed vial for 30 minutes at 140° C., providing a labelling yield of 60-80%.

Subsequently, the product was isolated by HPLC, trapped on a C-18 SepPak and recovered in 500 microliter of ethanol. This was then diluted with a citrate buffer and sterilized by filtration. The total synthesis time was approximately 2.5 hours with an overall yield of 40%. The radiochemical purity was 99.5 percent, measured the next day, and the specific activity was higher than 7.5 TBq per micromole. No precursor or other trace compounds were detected in the UV chromatogram.

EXAMPLE 3

Effect of Water on Labelling Yield

Figure 8:
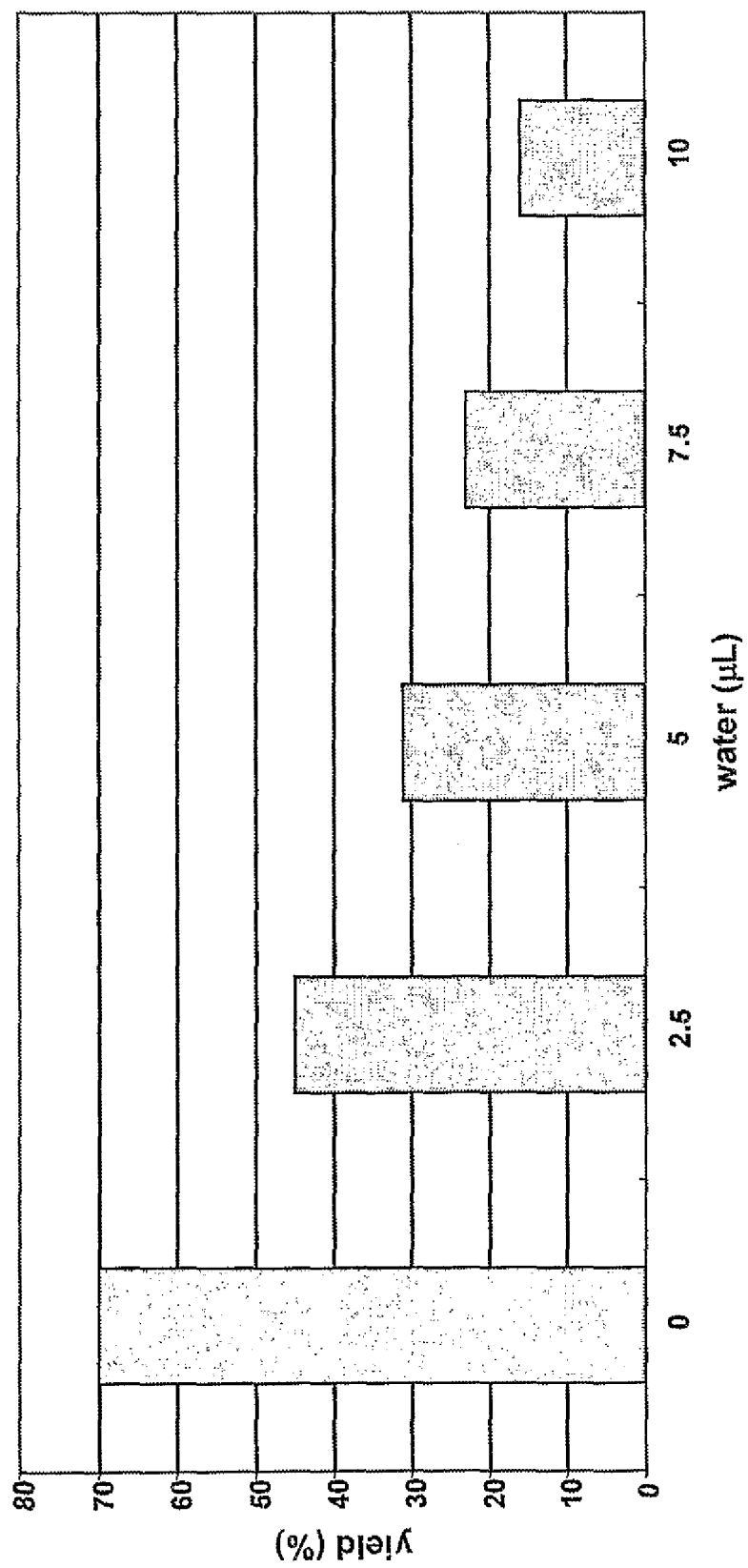
FIG. 8 shows a chart depicting the effect of water on labeling yield.

In order to determine the effect of water on the labelling yield of [$^{123}$I]iodocubane-WAY, increasing amounts of water up to 10% were added to the reaction mixture as described in EXAMPLE 2. FIG. 8 shows that water decreased the labelling yield dramatically.

EXAMPLE 4

Stability Testing

Figure 3:
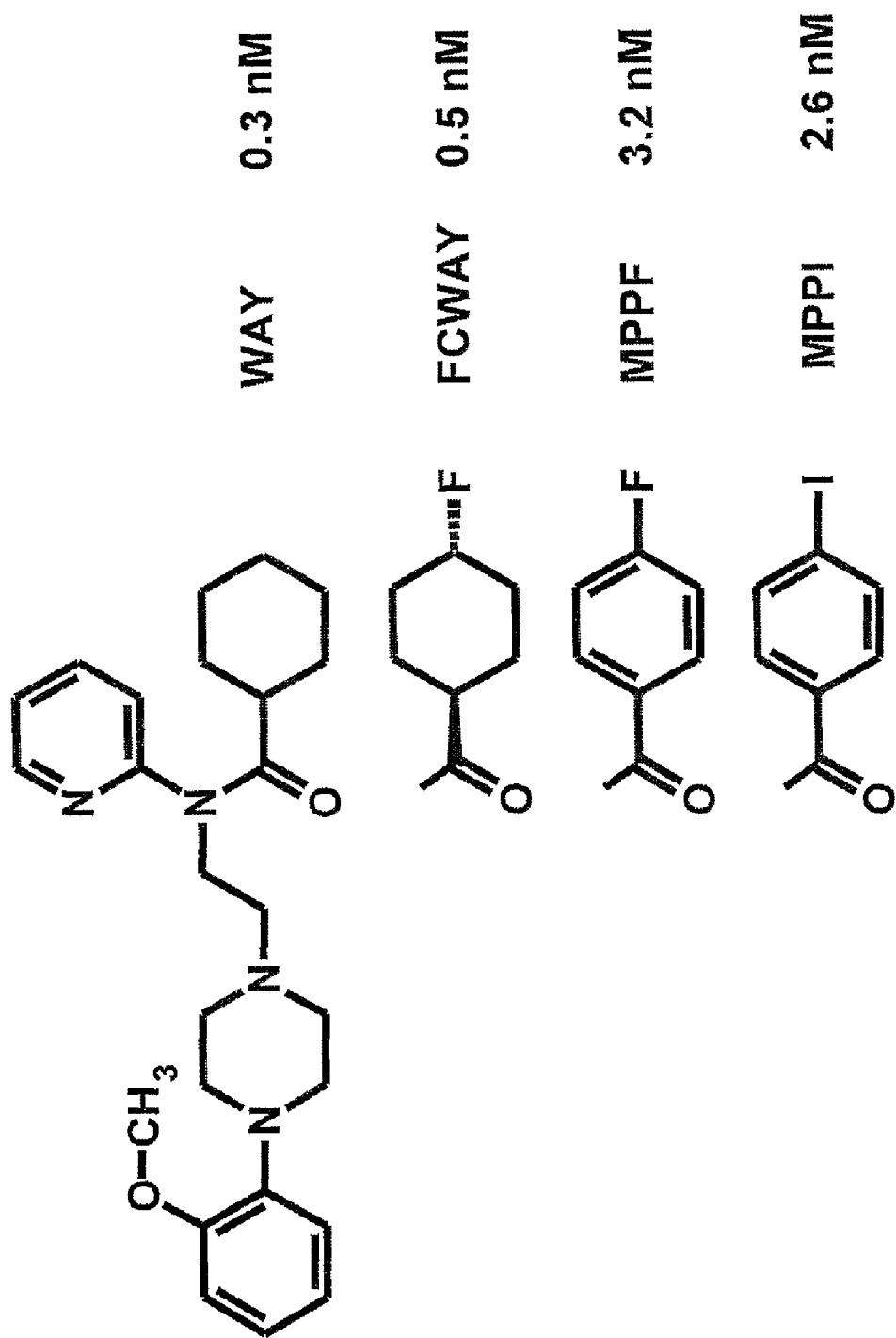
FIG. 3 shows exemplary derivatives of WAY-100635 labeled with Fluorine-18 ($t_{1/2}$=110 minutes) or Iodine-123 ($t_{1/2}$=13.2 hours).

[$^{123}$I]iodocubane-WAY was found to be completely stable in solution and in human plasma for at least 24 hours. In human hepatocytes a slow hydrolysis ($t_{1/2}$=75 min) of the amide bond was observed, but no de-iodination occurred. This was in contrast to MPPF (see FIG. 3) for which a half-life of approximately 15 minutes was found, together with a high de-fluorination rate.

In brief, cryopreserved human hepatocytes were thawed rapidly and diluted slowly with cell culture medium. After washing, the cell concentration was adjusted to 1 million per mL. [$^{123}$I]iodocubane-WAY (50 MBq) or [$^{18}$F]MPPF (50 MBq) was added. After 15, 60 and 150 minutes, a 200 microliter sample was taken, added to 200 microliters of methanol, sonicated and centrifuged. The metabolites in the supernatant were analyzed by HPLC. The results are shown in Table 4 below.

EXAMPLE 5

Affinity Testing

Relative binding affinities of the candidate 5-HT$_{1A}$ receptor tracers were determined in competitive binding assays (n=4 per tracer) using [$^3$H]8-OH-DPAT (Perkin Elmer, Boston, USA) as a reference. A membrane suspension from HEK-293 EBNA-cells expressing the human recombinant human 5-HT$_{1A}$ receptor subtype, was obtained from Perkin Elmer (Boston, USA). The protein concentration of the original suspension was 36.8 mg/mL.

Aliquots of these diluted membranes (factor 1:20) were incubated on microplates for 120 min at 37° C. in the dark. 200 µL assays were used, containing 20 µL of diluted membranes, a stable concentration of [$^3$H]8-OH-DPAT and candidate tracers in increasing concentrations (range $10^{-12}$ to $10^{-5}$). The incubation buffer contained 50 mM TRIS-HCl and 5 mM MgSO$_4$ (pH to 7.4 at 25° C.). The [$^3$H]8-OH-DPAT was used in a final concentration of 1.1 nM. The equilibrium dissociation constant (K$_D$) in nM of [$^3$H]8-OH-DPAT for the 5-HT$_{1A}$ receptor subtype was provided by the manufacturer (2.4 nM). Non-specific binding was determined using 5-hydroxytryptamine (5-HT, serotonin) as a competitor in a concentration of 10 µM.

After the incubation period, the reaction was rapidly terminated by vacuum filtration over a GF/C glass fiber filters that were incorporated in the microplates and that were pre-soaked in 0.5% polyethylenimine (Sigma-Aldrich, Munich, Germany), and washed 5 times with ice-cold TRIS-HCl buffer. 25 µL of scintillation fluid (MicroScint™, Perkin Elmer, Boston, USA) were added to each well, after which the microplates were counted in a liquid scintillation counter (Topcount, Packard).

For each candidate tracer, the inhibition constant (K$_i$) was calculated from the EC50 for the 5-HT$_{1A}$ receptor with non-linear regression curve fitting using the computer program Graphpad Prism® (version 3.02). The calculations for the receptor subtype were based on the K$_D$ of [$^3$H]8-OH-DPAT.

The results are shown in FIG. 6. The highest affinity was found for iodo-cubyl-WAY.

EXAMPLE 6

Biodistribution

[$^{123}$I]iodocubane-WAY (15 MBq) was injected into the tail vein of male Wistar rats (n=4) either with or without blocking of the HT$_{1A}$ receptor with a pre-dose of unlabelled WAY-100635. At 45 minutes p.i. rats were killed by cervical dislocation, tissue of interest was removed and counted for radioactivity.

Table 3 shows that, although uptake in cerebellum was still relatively high leading to low ratio's for the cortex and hippocampus, blocking studies clearly provided a reduction in the serotonin-1A rich regions, as all ratio's returned to unity. Furthermore, no uptake of radioactivity was found in the thyroid.

EXAMPLE 7

Labelling of Monoclonal Antibodies

Methyl-4-bromocubanecarboxylate (1.5 mg), Cu(II)triflate (0.01 mg) and N,N-dimethylpiperazine (0.1 mg) were added to a solution of nca [$^{123}$I]iodide (750 MBq) in 150 microliter of acetonitrile. This mixture was heated in a closed vial for 40 minutes at 140° C. [$^{123}$I]methyl-4-iodocubanecarboxylate (620 MBq, 83% radiochemical yield) was isolated from the precursor by HPLC, hydrolyzed and subsequently converted into a tetrafluorphenyl ester using a water-soluble carbodiimide (EDAC). The active ester (500 MBq) was trapped on a C-18 SepPak from which it was eluted with 0.5 mL of acetonitrile.

Addition of this TFP-ester to a buffered (pH=9.2) solution of the monoclonal antibody cetuximab (1 mg) using the method described by L R Perk et al. (J. Nucl. Med. (2005) 46, 1898-1906) resulted in a labelling yield of 60-80%.

EXAMPLE 8

Synthesis of [$^{123}$I]-(4-iodocubane-1-yl)-acetonitrile (4-Bromocubane-1-yl)-acetonitrile (1.5 mg), Cu(II)triflate (0.01 mg) and N,N-dimethylpiperazine (0.1 mg) were added to a solution of nca [$^{123}$I]iodide (100 MBq) in 150 microliter of acetonitrile. This mixture was heated in a closed vial for 40 minutes at 140° C. resulting in a near quantitative (98%) yield of [$^{123}$I]-(4-iodocubane-1-yl)-acetonitrile.

TABLE 1

| Relative rate of hydrolysis | | |
|---|---|---|
| X = Tosylate | calc. | exp. |
| tert-Butyl | 1 | 1 |
| 1-Adamantyl | $10^{-4}$ | $10^{-3}$ |
| 1-Bicyclo[2.2.2]octyl | $10^{-8}$ | $10^{-7}$ |
| 1-Norbornyl | $10^{-14}$ | $10^{-13}$ |
| Cubyl | $<10^{-25}$ | $10^{-10}$ |

TABLE 2

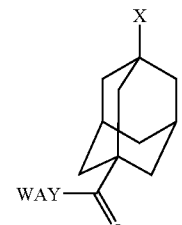

1

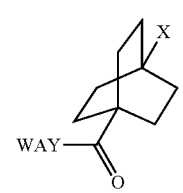

2

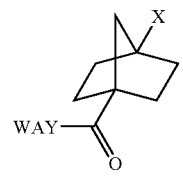

3

4

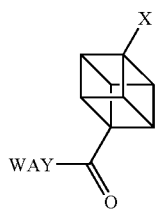

| Precursor | Product X = $^{123}$I | Radiochemical yield |
|---|---|---|
| 1 X = I | 1 | 40% |
| 2 X = I | 2 | 0% |
| 3 X = I | 3 | 1% |
| 4 X = I | 4 | 85% |
| 1 X = Br | 1 | 10% |
| 2 X = Br | 2 | 0% |
| 3 X = Br | 3 | 0% |
| 4 X = Br | 4 | 70% |

TABLE 3

BRAIN UPTAKE OF [$^{123}$I]CUBANE-WAY IN RATS

| Tissue | Unblocked | | | | Blocked[1] | | | |
|---|---|---|---|---|---|---|---|---|
| | Uptake[2] +/− SEM | | Ratio[3] +/− SEW | | Uptake[2] +/− SEM | | Ratio[3] +/− SEM | |
| Striatum | 9.4 | 0.8 | 0.91 | 0.02 | 9.2 | 0.6 | 0.86 | 0.02 |
| Cortex | 13.6 | 2.1 | 1.31 | 0.05 | 10.5 | 1.1 | 0.97 | 0.07 |
| Hippocampus | 25.2 | 5.0 | 2.49 | 0.31 | 11.9 | 1.7 | 1.08 | 0.07 |
| Cerebellum | 10.5 | 0.8 | | | 10.9 | 0.8 | | |

[1]Blocked with 0.4 mg of WAY-100635, 1 minute prior to injection of [$^{123}$I]cubane-WAY
[2]Percentage injected dose * times body-weight/per gram of tissue at 45 minutes
[3]Ratio indicates the uptake of the indicated tissue divided by the uptake of the cerebellum

TABLE 4

| | t = 0 | t = 15 | t = 60 | t = 150 |
|---|---|---|---|---|
| Iodocubane-WAY | 99.9% | 90.7% | 60.1% | 24.9% |
| Iodocubanecarboxylic acid | — | 9.0% | 39.7% | 74.9% |
| Free iodide | 0.1% | 0.3% | 0.2% | 0.2% |
| Unidentified compounds | 0% | 0% | 0% | 0% |
| MPPF | 99.2% | 45.2% | 22.7% | 8.4% |
| Fluorobenzoic acid | — | 24.8% | 41.8% | 50.1% |
| Free fluoride | — | 19.6% | 31.2% | 40.6% |
| Unidentified compounds | 0.8% | 11.4% | 4.3% | 0.9% |

What is claimed is:

1. A compound having the general formula:

Y-L-BFR-X wherein
BFR is a bridged fused ring system;
Y is a targeting group;
L is optionally present and is a linker for coupling Y to BFR; and
X is coupled to a bridgehead atom of BFR and is selected from the group consisting of:
halogens other than bromine and iodine;
a CH$_2$F group optionally labelled with $^{18}$F; and
—CH$_2$OSO$_2$R, —OSO$_2$R, —Sn(alkyl)$_3$ and —Pb(alkyl)$_3$, wherein R is selected from the group consisting of —CH$_3$, —CF$_3$, —(C$_6$H$_4$)CH$_3$, and —(C$_6$H$_4$)NO$_2$.

2. A compound having the general formula:

Y-L-BFR-X wherein
BFR is a bridged fused ring system other than an adamantane fused ring system;
Y is a targeting group;
L is optionally present and is a linker for coupling Y to BFR; and
X is selected from the group consisting of halogen, a CH$_2$F group optionally labelled with $^{18}$F, —OH, —CH$_2$OSO$_2$R, —OSO$_2$R, —Sn(alkyl)$_3$ and —Pb(alkyl)$_3$, wherein R is selected from the group consisting of —CH$_3$, —CF$_3$, —(C$_6$H$_4$)CH$_3$, and —(C$_6$H$_4$)NO$_2$, wherein X is coupled to a bridgehead atom of BFR.

3. The compound of claim 2, wherein X is selected from the group consisting of $^{123}$I, $^{124}$I, $^{131}$I, $^{76}$Br, $^{77}$Br, and $^{82}$Br.

4. The compound of claim 2, wherein X is $^{123}$I.

5. The compound of claim 2, wherein X is —OH, —Br or —I.

6. The compound of claim 2, wherein BFR is selected from the group consisting of bicyclooctane, norbornane and cubane.

7. The compound of claim 2, wherein BFR is cubane.

8. The compound of claim 2, wherein X is non-radioactive.

9. The compound of claim 2, wherein X is radioactive.

10. The compound of claim 9, wherein X is $^{18}$F or $^{211}$At.

11. The compound of claim 2, wherein X is selected from the group consisting of —OSO$_2$R, —Sn(alkyl)$_3$ and —Pb(alkyl)$_3$, and wherein R is selected from the group consisting of —CH$_3$, —CF$_3$, —(C$_6$H$_4$)CH$_3$, and —(C$_6$H$_4$)NO$_2$.

12. The compound of claim 2, wherein X is a CH$_2$F group optionally labelled with $^{18}$F.

13. The compound of claim 2, wherein X is —CH$_2$OSO$_2$R, and wherein R is selected from the group consisting of —CH$_3$, —CF$_3$, —(C$_6$H$_4$)CH$_3$, and —(C$_6$H$_4$)NO$_2$.

14. The compound of claim 2, wherein L is present and is selected from the group consisting of —(CO)—, —O(CO)—, —NH(CO)—, —NH—, —O(CH$_2$)$_n$—, —NH(CH$_2$)$_n$—, —NH(CO)NH—, and —NH(CS)NH—.

15. The compound of claim 2, wherein BFR is a bridged fused ring system having a skeleton of only carbon atoms.

16. The compound of claim 2, wherein BFR is a bridged fused ring system comprising at least one heteroatom.

17. The compound of claim 2, wherein Y is selected from group consisting of amino acids, peptidomimetics, nucleic acids, RNA, DNA, nucleosides, nucleotides, carbohydrates, glycomimetics, lipids, phospholipids, hormones, neurotransmitters, and vitamins.

18. The compound of claim 2, wherein the compound has the formula:

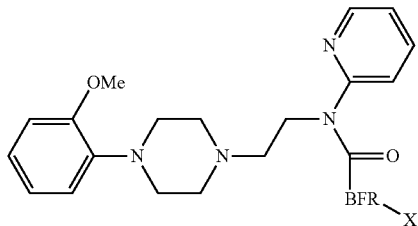

wherein BFR and X are as defined in claim 2.

19. The compound of claim 17, wherein Y is N-(2-(4-(2-methoxyphenyl)piperazin-1-yl)ethyl)pyridin-2-amine.

20. The compound of claim 2, wherein Y is selected from group consisting of proteins, peptides, enzymes, antibodies and fragments thereof.

21. The compound of claim 2, wherein Y is selected from group consisting of polyaminoacids, polyols, polyamines, polyacids, oligonucleotides, aborols, dendrimers and aptamers.

* * * * *